United States Patent [19]

Chan et al.

[11] Patent Number: 4,758,586
[45] Date of Patent: Jul. 19, 1988

[54] INDOLYL COMPOUNDS AND HYPOSENSITIVITY USE THEREOF

[75] Inventors: Wan-kit Chan, Pound Ridge; Thomas D. Lee, Scarsdale, both of N.Y.; Fu-chih Huang, Leonia, N.J.

[73] Assignee: USV Pharmaceutical Corp., Fort Washington, Pa.

[21] Appl. No.: 821,063

[22] Filed: Jan. 21, 1986

Related U.S. Application Data

[63] Continuation-in-part of Ser. No. 697,594, Feb. 1, 1985, abandoned.

[51] Int. Cl.$^4$ .................... C07D 209/12; A61K 31/40
[52] U.S. Cl. .................................. 514/415; 514/419; 548/494; 548/509
[58] Field of Search ................ 548/494, 509; 514/419, 514/415

[56] References Cited

U.S. PATENT DOCUMENTS 3,271,416  9/1966  Shen et al. ......................... 548/492
4,536,505  8/1985  Browne ............................. 546/273

*Primary Examiner*—Glennon H. Hollrah
*Assistant Examiner*—D. B. Springer

[57] ABSTRACT

Indolyl dieneoic acids and esters are disclosed possessing valuable pharmaceutical activity, particularly as lipoxygenase inhibitors with anti-inflammatory and anti-allergic properties.

24 Claims, No Drawings

INDOLYL COMPOUNDS AND HYPOSENSITIVITY USE THEREOF

This application is a continuation-in-part of U.S. patent application, Ser. No. 697,594, filed Feb. 1, 1985, abandoned.

This invention relates to new chemical compounds possessing valuable pharmaceutical activity, particularly as lipoxygenase inhibitors possessing anti-inflammatory and antiallergic properties. The present new compounds are of

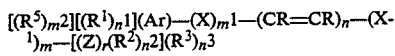  (I)

and salts thereof where $R^1$ is independently hydrogen, alkyl, aryl, hydroxyalkyl, carboxy, carbalkoxy, carbamoyl, alkylenecarboxy, arylenecarboxy, alkylenecarbalkoxy, alkanoyl, formyl, nitrilo, amino, aminoalkylene, alkylamino, carboxamide, halo, trihalomethyl, hydroxy, alkoxy, aralkoxy, aryloxy, nitro, sulfamoyl, mercapto or alkylthio;

$R^5$ is alkyl, hydroxyalkyl, carboxyl, aryl, carbamoyl, carbalkoxy, alkanoyl, nitrilo, amino, alkylamino, halo, trihalomethyl, aryloxy, nitro, sulfamyl, mercapto or alkylthio;

Ar is phenyl, naphthyl or a nitrogen, oxygen or sulfur containing heterocyclic or benzoheterocyclic ring;

X is alkylene containing up to 4 carbon atoms in the principal chain and up to a total of 8 carbon atoms;

R is hydrogen, alkyl or halo;

$X^1$ is oxygen, sulfur or $-NR^4$;

Z is alkylene containing up to 10 carbon atoms in the principal chain and up to a total of 12 carbon atoms including from 0 to 2 double bonds;

$R^2$ is a substituent attached to one of the carbons of Z and is oxo, $-OR^4$, $-SR^4$, $-N(R^4)_2$, $-COOR^4$ or $-CON(R^4)_2$;

$R^3$ is hydrogen, cycloalkyl, carboxy, $-OR^4$, $-N(R^4)_2$, trifluoromethyl, dialkylamino, carbalkoxy or aryl;

$R^4$ is hydrogen, alkyl, benzoyl, alkanoyl, aryl or aralkyl;

m is 0 or 1;
$m^1$ is 0 or 1;
$m^2$ is 0 or 1;
n is 1 or 2;
$n^1$ is 1, 2 or 3 if Ar is not phenyl; if Ar is phenyl, $n^1$ is 1 or 3;
$n^2$ is 1 or 2;
$n^3$ is 0, 1 or 2; and
r is 0 or 1.

Within the generic class of compounds of the present invention are the subgeneric compounds of the formulas:

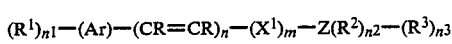  (II)

or

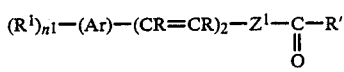  (III)

and salts thereof; wherein

Ar is a nitrogen, oxygen or sulfurheterocyclic ring or a benzoheterocyclic ring;

each R is independently hydrogen, alkyl, aryl, carboxy, carbalkoxy, alkylenecarboxy, arylenecarboxy, alkylenecarbalkoxy, alkanoyl, formyl, nitrilo, amino, aminoalkylene, alkylamino, carboxamide, halo, trihalomethyl, hydroxy, alkoxy, aralkyloxy, aryloxy, nitro, sulfamyl, mercapto or alkylthio;

each R is H or alkyl;

$X^1$ is oxygen, sulfur or $-NR^4$;

Z is an alkylene chain containing up to 10 carbon atoms in the principal chain and up to a total of 12 carbon atoms containing 0 to 2 double bonds;

each $R^2$ is a substituent attached to the carbon atom adjacent to the olefinic bond of Z selected from the group consisting of oxo, $OR^4$, $-SR^4$, $-N(R^4)_2$, $-CHO$ and $-COR^5$;

each $R^4$ is hydrogen, alkyl, benzoyl, lower alkanoyl, aryl or aralkyl;

$R^5$ is $OR^4$ or $N(R^4)_2$;

each $R^3$ is hydrogen, cycloalkyl, aralkyl, aryl, $CF_3$ or dialkylamino;

$Z^1$ is an alkylene chain containing from 0-10 carbon atoms in the principal chain and up to a total of 12 carbon atoms and from 0 to 2 double bonds;

R' is H or $R^5$;
m=0 or 1;
n=1 or 2;
$n^1$=1 or 2;
$n^2$=1 or 2; and
$n^3$=1 or 2.

The group Ar is a heterocyclic ring which contains at least one oxygen, sulfur or nitrogen and includes the so-called benzoheterocyclic rings. Exemplary heterocyclics include pyrrole, pyridine, thiophene, thiazole, oxazole, benzofuran, quinoline, indole, benzothiophene, benzoxazole and similar heterocyclic rings as well as the N-oxides of the nitrogen heterocycles. Ar is preferably quinoline, indole, benzofuran, pyridine or benzothiophene. The indole may be N-substituted with $R^6$ wherein $R^6$ is hydrogen, lower alkyl, lower alkenyl, $C_4$–$C_8$ cycloalkyl, $C_4$–$C_8$ cycloalkenyl, aryl, aryllower-alkyl, araloweralkenyl, loweralkylcarbonyl, arylcarbonyl, araloweralkylcarbonyl, araloweralkenylcarbonyl, pyridylloweralkyl or quinolylloweralkyl.

The alkyl groups, either alone or within the various substituents defined hereinbefore are preferably lower alkyl, which may be straight or branched chain and include methyl, ethyl, propyl, isopropyl, butyl, isobutyl, amyl, hexyl and the like.

The halo atoms in halo and trihalomethyl are Cl, Br, I or preferably F. The aryl groups are preferably phenyl or naphthyl.

The aryl groups, i.e., phenyl, the aryl group of arylalkyl, and benzoyl, may be unsubstituted or substituted with one or two substituents such as OH, alkoxy, aryloxy, arylalkyloxy, halogen, alkyl, carboxy, carbalkoxy, carboxamide and similar such groups.

The stereochemistry about the double bonds in formulae II and III is either in the E or Z configuration.

The preferred compounds of Formula II are those in which $R^2$ is $OR^4$, n is 1, $n^2$ is 1 and Z contains up to five carbon atoms in the principal chain and is attached directly to $(CR=CR)_n$ by a covalent bond.

The present invention also relates to therapeutic compositions having the above formulas wherein R', $R^1$, Ar, R, Z, $R^2$, $R^3$, $R^4$, $R^5$, n, $n^1$, $n^2$, $n^3$ are defined hereinabove. Finally, the present invention also relates to the use of these compounds as therapeutic reagents possessing anti-inflammatory and anti-allergic properties.

Compounds similar to, but distinguished from, the generic class of Formula III are known in the art. For example, ethyl β-(indol-3-yl) acrylate

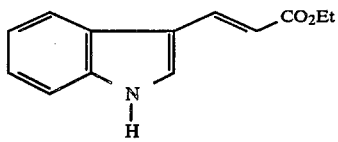

which was synthesized by Piozzi and Funganti (see, Ann. Chem., 57(5), 486–491 (1969)) was found only the have antimicrobiol activity by Whitehead and Whitesitt. (See, Journal of Medicinal Chemistry, 17(12), 1298–1304 (1974)). Also, the preparation of ethyl 1-benzylindol-3-yl-acrylate

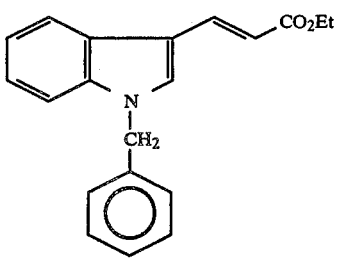

as well as ethyl 3-(2-methylindol-3-yl)-3-phenyl-2-priopionate

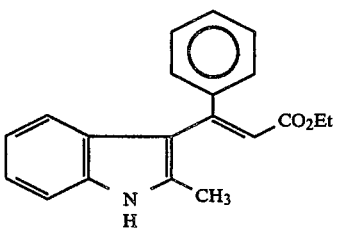

are described in Germ Offen. No. 2,059,386 (1971).

The preferred compounds of Formula III are those in which n is 2, $n^2$ is 1 and Z contains 0 to 6 carbon atoms, none of which have been previously described or synthesized.

The new compounds of Formulae II and III are prepared by art recognized procedures from known starting compounds. The following procedure is exemplary in which the carbonyl group of reactant IV condenses with the active methylene of reactant V and VI:

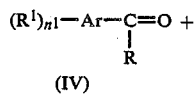

(IV)

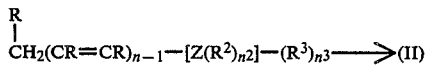

(V)

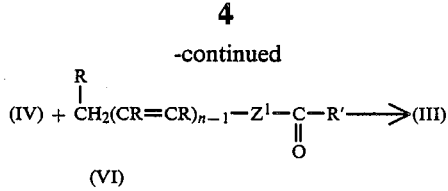

The condensation of compound IV, with each of compound V and VI, can be carried out in the presence of a metal hydride, commonly sodium hydride, and is facilitated by providing the formula V and VI compounds in the form of the dialkylphosphono or triphenylphosphido derivative on the reactive methylene group.

The reaction is conveniently carried out in a solvent which is, of course, non-reactive under reaction conditions employed, usually at room temperature, although temperatures up to the reflux temperature of the reaction mixture can also be used. Suitable dimethyl formamide, dimethylacetamide and the like. Usually, it is preferred to employ compounds of formula VI in which R' is an alkoxy, i.e., the ester form, from which after condensation, the other functional groups in which R' is hydrogen, i.e., the aldehyde, —OH, i.e., the free carboxy group and $N(R^4)_2$, i.e., the amide, can be formed by classical methods.

Many variations of this procedure can be used to form various derivatives represented by $R^2$ in Formula II compounds. For example, the corresponding compounds of Formula III can be converted to those of Formula I by appropriate classical reactions. For example, compounds of Formula III in which R' is H or $OR^4$, i.e., the aldehyde or the ester, are converted to compounds of formula II in which $R^2$ is hydroxy by reaction of the aldehyde group with a Grignard reagent to form a secondary alcohol or reduction of ester group to a primary alcohol. Thus, many of the compounds of Formula III serve as intermediates in the preparation of compounds of Formula II and are useful for this purpose in addition to their use as therapeutic compounds.

Some of the final products of Formulae II and III can be further treated to form other analogous compounds by, for example, removal of benzyl groups by hydrogenolysis, i.e., benzyloxy to hydroxy, substitution and coversion reations, i.e., nitro to amino by classical reduction and nitrile to carboxyl by hydrolysis.

Another subgeneric class of compounds within the contemplation of the instant invention are a class of homocinnamyl alcohols, also possessing hyposensitivity properties, having the structural formula

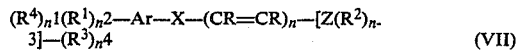

and salts thereof wherein
Ar is phenyl, naphthyl, or a nitrogen, oxygen, or sulfur heterocyclic ring;
each $R^1$ is independently hydrogen, lower alkyl, aryl, hydroxy, hydroxy-lower alkyl, lower alkanoyl, halo, benzyloxy, trihalomethyl, lower alkoxy, aryloxy, aryl-lower alkoxy, nitrilo, carboxy, carbo-lower alkoxy, carbamoyl, amino, lower alkylamino, di-lower-alkylamino, mercapto, lower alkylthio, nitro, or sulfamyl;
each R is hydrogen, alkyl, or halo;
each $R^4$ is lower alkyl, hydroxy-lower alkyl, lower alkanoyl, halo, trihalomethyl, aryloxy, nitrilo, carboxy, carboloweralkoxy, carbamoyl, amino, lower alkylamino, di-lower-alkylamino, mercapto, lower alkylthio, nitro or sulfamyl;

X is an alkylene chain containing up to 4 carbon atoms in the principal chain and up to a total of 8 carbon atoms;

Z is an alkylene chain containing up to 10 carbon atoms in the principal chain and up to a total of 12 carbon atoms and from 0 to 2 double bonds or Z when taken together with the carbon atoms of $(CR=CR)_n$ to which it is attached forms a cycloalkylidene ring;

each $R^2$ is a substituent attached to one of the carbon atoms of Z and is $OR^5$;

each $R^3$ is hydrogen, cycloloweralkyl, aryl, $CF_3$, diloweralkylamino, carboxy or carboloweralkoxy;

each $R^5$ is hydrogen, lower alkyl, benzoyl, loweralkanoyl, aryl or loweraralkyl;

n=1 or 2;

$n^2$=1, 2, or 3 when Ar is other than phenyl; but $n^2$=1 or 3 when Ar is phenyl;

$n^3$=1 or 2;

$n^4$=1 or 2 and $n^1$=0 or 1;

with the proviso that when Ar is phenyl, and n, $n^3$ and $n^4$=1, Ar cannot be unsubstituted phenyl or hydroxyphenyl.

Alcohols structurally similar to but distinguished from the compounds of Formula VII are known in the art. European Patent Application 125,919 to Yamanouchi Pharmaceutical K.K. discloses a class a cinnamyl alcohols, rather than the homocinnamyl alcohols of the present invention.

G. C. M. Aithic et al., *Tet. Letters*, 4419 (1975) describes the synthesis of the following unsaturated alcohols:

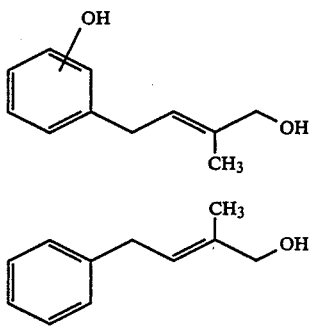

Compounds of Formula VII can be synthesized by the reaction of the appropriate aryl-Grignard reagent or aryl-lithium salt and an allyl epoxide. This reaction is as follows:

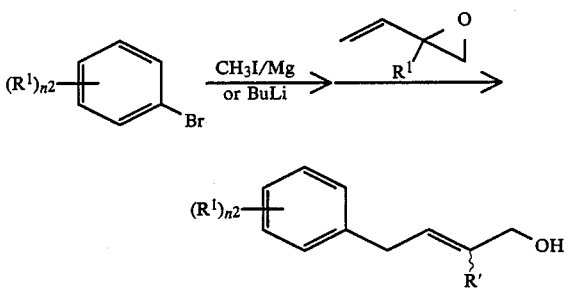

The alcohol thus obtained can be oxidized to aldehyde which can be then coupled with a ketone. Hydride reduction of the aldol condensation product would yield another product within the meaning of Formula VII wherein n=2.

Alternatively, an arylacetaldehyde and a ketone can be reacted in basic medium to afford a keto product, which upon hydride reduction would yield the desired alcohol within the meaning of Formula VII.

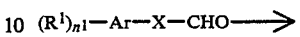

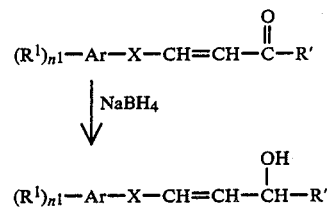

The present new compounds form salts with acids when a basic amino function is present and salts with bases when an acid function, i.e., carboxyl, is present. All such salts are useful in the isolation and/or purification of the new products. Of particular value are the pharmaceutically acceptable salts with both acids and bases. Suitable acids include, for example, hydrochloric, sulfuric, nitric, benzenesulfonic, toluenesulfonic, acetic, malic, tartaric and the like which are pharmaceutically acceptable. Basic salts for pharmaceutical use are the Na, K, Ca and Mg salts.

The compounds of the present invention can be administered to the host in a variety of forms adapted to the chosen route of administration, i.e., orally, intravenously, intramuscularly or subcutaneous, topically or inhalation routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch, or gelatin; excipients such as dicalcium phosphate; a disintegrating agent such as corn starch, potato starch, alginic acid and the like; a lubricant sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that each syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The following examples further illustrate the invention.

EXAMPLE 1

Ethyl 5-(1-Benzylindol-3-yl)-2,4-Pentadienoate

To a suspension of 1.08 g (60% reagent, 27 mmol) of sodium hydride in 20 ml of tetrahydrofuran (THF), stirred in an ice bath, was added dropwise 6 ml (6.7 g, 27 mmol) of triethyl 4-phosphonocrotonate. The resulting mixture was stirred for an additional 1 hour in the cooling bath and a solution of 4.2 g (18 mmol) of 1-benzylindol-3-carboxaldehyde in 25 ml of water. This mixture was transferred to a separatory funnel and the layers were separated. The aqueous layer was extracted with two 50 ml portions of ethyl acetate. The combined organic layer was washed with two 25 ml portions of brine, dried (magnesium sulfate) and concentrated on a rotary evaporator to give an oil. Purification on a dry column (25% ethyl acetate in hexane) followed by crystallization (acetone-ether) gave 3.7 g of product as orange crystals, m.p. 110–112. MS (EI): 331 (M+), 240 (M+—$C_7H_7$), 167 (M+—$C_7H_7$—$CO_2C_2H_5$). NMR spectrum ($CDCl_3$) shows a triplet centered at $\delta 1.26$ (J=7 Hz), a singlet at $\delta 5.21$, a doublet centered at $\delta 5.8$ which is the signal of the olefinic proton adjacent to the carbonyl group. The remainder of the proton signals cluster around 7.25 ppm.

EXAMPLE 2

5-(1-Benzylindol-3-yl)-2,4-Pentadienoic Acid

To a solution of 1.2 g (3.6 mmol) of ethyl 5-(1-benzylindol-3-yl)2,4-pentadienoate in 250 ml of ethanol was added with stirring at room temperature a solution of 1 g (19 mmol) of potassium hydroxide in 5 ml of water. The resulting mixture was stirred four days. Most of the ethanol was removed on a rotary evaporator; the concentrated reaction mixture was taken up in 150 ml of water, washed with two 30 ml portions of ethyl acetate and acidified to pH 3 with 1N aqueous HCL. The yellow precipitate was extracted with ethyl acetate, washed with two 30 ml portions of water, dried ($MgSO_4$) and concentrated on rotary evaporator to afford 1 g of product. Crystallization from ethyl acetate gave orange crystals, m.p. 194–196. MS(EI): 259 (M+$CO_2$), 258 (M+—$CO_2H$); nmr ($CDCl_3$): $\delta 5.30$ (s, 2), $\delta 5.76$ (d, J=15 HZ, 1), other proton signals appear between $\delta 6.8$ to $\delta 7.8$.

EXAMPLE 3

N-(4-Carbethoxyphenyl)-5-(1-benzylindol-3-yl)-2,4-Pentadienamide

To a suspension of 5-(1-benzylindol-3-yl)-2,4-pentadienoic acid (0.9 g, 2.9 mmol) in 20 ml of methylene chloride was added dropwise with stirring at room temperature 0.26 ml (0.38 g, 3 mmol) of oxalyl chloride, followed by four drops of N,N-dimethyl-formamide (DMF). The reaction mixture was stirred for an additional 90 min. and concentrated on rotary evaporator. The residue was dissolved in 10 ml of anhydrous methylene chloride and added dropwise to a solution of ethyl p-aminobenzoate (0.44 g, 2.7 mmol) in 5 ml of methylene chloride and 1.3 ml of pyridine. The resulting mixture was stirred at room temperature for 18 hours and washed with saturated aqueous sodium bicarbonate solution and water, dried ($MgSO_4$) and mixture. Purification by a dry column (hexane:ethyl acetate, 2:1) followed by crystallization (acetone-petroleum ether) afforded 250 mg of yellow crystals, m.p. 162–166. MS(EI)=450(M+), 286 (M+—$HNC_6H_4CO_2C_2H_5$); nmr ($CDCl_3$): $\delta 1.35$ (t, J=7 Hz, 3), $\delta 4.28$(q, J=7 Hz, 2), $\delta 5.22$(s, 2), $\delta 5.95$(d, J=15 Hz, 1).

EXAMPLE 4

Ethyl 5-(1-Benzyl-5-Benzyloxyindol-3-yl)-2,4-Pentadienoate

In a manner similar to Example 1, 4 g (15 mmol) of 1-benzyl-5-benxyloxyindole-3-carboxaldehyde was treated with 20 mmol of triethyl phosphonocrotonate to afford, after dry column chromatography (hexane:ethyl acetate, 2:1) and crystallization (ether), 1.2 g of product as yellow crystals, m.p. 130–131. MS(EI): 437(M+), 346 (M+—$C_7H_7$), 273 (M+—$C_7H_7$—$CO_2Et$); nmr ($CDCl_3$): $\delta$1.22 (t, J=6 Hz, 3), $\delta$4.08 (q, J=6 Hz, 2), $\delta$5.10 (s, 2), $\delta$5.21 (s, 2), $\delta$5.80 (d, J=15 Hz, 1); other proton signals appear between $\delta$6.72 and $\delta$7.35.

EXAMPLE 5

5-(1-Benzyl-5-Benzyloxyindol-3-yl)-2,4-Pentadienoic Acid

In a manner similar to Example 2, 1 g (2.4 mmol) of ethyl 5-(benzyl-5-benzyloxyindol-3-yl)-2,4-pentadienoate was treated with 0.5 g (8.6 mmol) of potassium hydroxide in ethanol-water to give, after powders, m.p. 202–203. MS(EI): 365 (M+—$CO_2$), 274 (M+—$CO_2$—$CH_2C_6H_5$); NMR (DMSO-$d_6$): $\delta$5.14 (s, 2), $\delta$5.36 (s, 2), $\delta$5.89 (d, J=15 Hz, 1).

EXAMPLE 6

Ethyl 5-(1-Benzyl-5-Methoxyindol-3-yl)-2,4-Pentadienoate

In a manner similar to Example 1, 2.65 g (10 mmol) of 1-benzyl-5-methoxyindole-3-carboxyaldehyde) was treated with triethyl phosphonocrotonate to afford, after dry column chromatography (25% ethyl acetate in hexane), 3.2 g of product as yellow powders. This substance can be further purified by crystallization from ether to give yellow crystals, m.p. 93–96. MS(EI): 361 (M+), 288 (M+—$CO_2Et$), 270 (M+—$CH_2C_6H_5$). nmr ($CDCl_3$): $\delta$1.30 (t, J=7 Hz, 2), $\delta$3.86 (s, 3), $\delta$4.18 (q, J=7 Hz, 2), $\delta$5.18 (s, 2), $\delta$5.86 (d, J=15 Hz, 1), $\delta$7.46 (dd, J=15 Hz, 10 Hz).

EXAMPLE 7

5-(1-Benzyl-5-methoxyindol-3-yl)-2,4-Pentadienoic Acid

In a manner similar to Example 2, 1.8 g (5 mmol) of ethyl 5-(1-benzyl-5-methoxyindol-3-yl)-2,4-pentadienoate was hydrolyzed to give the acid as yellow powders. Crystallization in ethanol gave 1.3 g of yellow needles, m.p. 168 (decomp.) MS(EI): 333 (M+), 289 (M+—$CO_2$), 282 (M+—$CO_2H$), 242 (M+—$C_7H_7$), 198 (M+—$CO_2$—$C_7H_7$); nmr ($CDCl_3$/DMSO-$d_6$): $\delta$3.70 (s, 3), $\delta$5.14 (s, 2), $\delta$5.67 (d, J=15 Hz, 1); rest of the signals appear between $\delta$6.5 to $\delta$7.4.

EXAMPLE 8

Ethyl 5-(1-Benzylindol-3-yl)-2-Ethyl-2,4-Pentadienoate

A mixture of 5 g (19 mmol) of 1-benzyloxy-3-(3-hydroxy-1 propen-1-yl) indole and 25 g of activated manganese dioxide in 500 ml of dichloromethane was stirred at room temperature for three hours and filtered through Celite®. The manganese compound was washed thoroughly with a mixture of dichloromethane and ethyl acetate until the Celite® layer was colorless. The combined filtrate and washing were concentrated on rotary evaporator and the residue was purified on a dry column (25% ethyl acetate in hexane) to give 2.3 g of 3-(1-benzylindol-3-yl)acrolein.

In a manner similar to Example 1, 2.3 g (8 mmol) of the aldehyde was treated with 2.5 g (10 mmol) of triethyl 2-phosphonobutyrate. Purification of the crude product by dry column chromatography (hexane:ethylacetate, 2:1) afforded 1.8 g of pure ester as yellow powders, m.p. 100–102. In analytical tlc (25% ethyl acetate in hexane), this material appears in two spots, $R_f$=0.70 and $R_f$=0.65, corresponding to the 2Z and 2E isomers, respectively, MS(EI)=359 (M+), 334 (M+—$C_2H_5$); nmr spectrum shows the methylene protons of ethyl group as two sets of quartet (J+7.4 Hz) centered at $\delta$2.35 and $\delta$2.17, respectively, in a ratio of approximately 2:1.

EXAMPLE 9

5-(1-Benzylindol-3-yl)-2-Ethyl-2,4-Pentadienoic Acid

In a manner similar to Example 2, 1.8 g (5 mmol) of ethyl 5-(1-benzylindol-3-yl)-2-ethyl-2,4-pentadienoic acid was hydrolyzed to give the corresponding acid, m.p. (ether): 169–170. NMR ($CDCl_3$/DMSO-$d_6$) spectrum shows broad triplet and quartet at $\delta$1.10 and $\delta$2.47 respectively; the benzyl methylene signal appears at $\delta$5.30 as a broad singlet.

EXAMPLE 10

Ethyl 5-(indol-3-yl)-2,4-Pentadienoate a. In a manner similar to Example 1, 2.2 g (7.75 mmole) of 1-p-chlorobenzoylindole-3-carboxaldehyde was treated with triethyl phosphonocrotonate to give 4.8 g of crude mixture as a red oily substance. Purification by dry column chromatography (hexane:ethyl acetate; 2:1) followed by trituration in ether afforded 0.65 g of the product as yellow powders, m.p. 150–151. MS(EI): 241 (M+), 168 (M+—$CO_2Et$); nmr ($CDCl_3$): $\delta$1.32 (t, J=7.5 Hz, 3), $\delta$4.18 (q, J=7.5 Hz, 2), $\delta$5.86 (d, J=15 Hz, 1).

b. This compound was also prepared by debenzylation of ethyl 5-(1-benzylindol-3-yl)-2,4-pentadienoate by hydrogenolysis.

EXAMPLE 11

Ethyl 5-(1-Benzyl-2-methylindol-3yl)-2,4-Pentadienoate

In a manner similar to Example 1, 5 g (20 mmol) of 1-benzyl-2-methylindole-3-carboxaldehyde was reacted with triethyl phosphonocrotonate to give, after dry column chromatography (hexane:ethyl acetate, 2:1) and trituration from ether, 3.1 g of ethyl 5-(1-benzyl-2-methylindol-3-yl)-2,4-pentadienoate, m.p. 117–118. MS(EI)=345 (M+), nmr ($CDCl_3$): $\delta$1.34 (t, J=7.5 Hz, 3), $\delta$2.43 (s, 3), $\delta$4.20 (q, J=7.5 Hz, 2), $\delta$5.24 (s, 2), $\delta$6.40 (d, J=15 Hz, 1).

EXAMPLE 12

5-(1-Benzyl-2-methylindol-3-yl)-2,4-Pentadienoic Acid

In a manner similar to Example 2, 2.5 g (7.2 mmol) of ethyl 5-(1-benzyl-2-methylinol-3-yl)-2,4-pentadienoate was hydrolyzed to give, after trituration in ether, 1.4 g of the acid as yellow powders, m.p. 146–148. MS (EI): 317 (M+); nmr (DMSO-$d_6$): $\delta$2.44 (s, 3), $\delta$5.3 (s, 2), $\delta$6.30 (d, J=15 Hz, 1).

EXAMPLE 13

1-Benzyl-3-(3-Hydroxy-1-Propen-1-yl)Indole

To a solution of 4.7 g (15 mmol) of ethyl 3-(1-benzylindol-3-yl)acrylate in 300 ml of diethyl ether, stirred in an ice bath, was added in portions 1.6 g (0.03 mol) of lithium aluminum hydride (LAH). The resulting mixture was stirred for 10 min. and quenched by adding dropwise 2.2 ml of water. The mixture was filtered through a patch of Celite ® and the residue was washed with 200 ml of ethyl acetate. The combined filtrate and washing was washed once with water, dried (magnesium sulfate) and concentrated on rotary evaporator to afford a yellow oil. Recrystallization from ether gave 1.6 g of pure product. MS(EI): 263 (M+), 245 (M+—H$_2$O), 154 (M+—H$_2$)—C$_6$H$_5$CH$_2$). The nmr spectrum (CDCl$_3$) shows a singlet at 5.2 and a doublet (J=6 Hz) at 4.24 ppm.

EXAMPLE 14

5-(1-Benzylindol-3-yl)2,4-Pentadien-1-al

To a solution of ethyl 5-(1-benzylindol-3yl)-2,4-pentadienoate (1.5 g, 4.5 mmol) in 100 ml of diethyl of diethyl ether and 20 ml of tetrahydrofuran, stirred at 0° C. (ice bath), was added in portions 0.34 g (9 mmol) of LAH; the resulting mixture was stirred at room temperature for 26 hours, and worked up in manner similar to Example 13 to afford, after purifications by dry column chromatography (2:1, hexane:ethyl acetate), 1.2 g of the intermediate 2,4-pentadienol. This substance was dissolved in 250 ml of dichoromethane and 6 g of activated manganese dioxide was added. The suspension was stirred at room temperature for 6 hours. Manganese dioxide was removed by filtering through Celite ® and washed thoroughly with a mixture of ethyl acetate and methylene chloride. The combined filtrate and washing were concentrated on a rotary evaporator to give 1 g of the product as an orange colored oil. This substance was used without purification in Example 15. NMR spectrum shows a singlet a 5.18 ppm and a doublet (J=7.5 Hz) at 9.48 ppm.

EXAMPLE 15

1-Benzyl-3-(5-Hydroxy-1,3-Decadien-1-yl)-Indole

To a solution of 5-(1-benzylindol-3-yl)-2,4-pentadienal (2 g, 7 mmol) in 25 ml of tetrahydrofuran, stirred in a dry ice-acetone bath, was added in one portion 7 mmol of n-pentyl magnesium bromide (3.9 ml of 1.8M solution in ether). The resulting mixture was stirred at −78° C. for 90 min. and then mixed with 50 ml of water after warming up to about 0° C. Ethyl acetate, 50 ml, was added and the layers were separated. The organic layer was washed with water, dried (MgSO$_4$) and concentrated on rotary evaporator to give the crude mixture. This substance was purified on a silica gel dry column (25% ethyl acetate in hexane) to afford 0.4 g of the produce as an oil. NMR spectrum shows a singlet at 5.12 and a multiplet centered at 4.05 ppm.

EXAMPLE 16

Ethyl 5-(5-methoxyindol-2-yl)-2,4-Pentadienoate

In a manner similar to Example 1, 2.8 g (0.016 mol) of 5-methoxyindole-2-carboxyaldehyde was treated with 0.024M of triethyl phosphonocrotonate to afford, after dry column chromatography (25% ethyl acetate in hexane) and crystallization (acetone-diethyl ether), 2.5 g of ethyl 5-(5-methoxyindol-2-yl)-2,4-pentadienoate as yellow powders, m.p. 168°–170° C. MS(EI): 261 (M+), 198 (M+—CO$_2$Et).

EXAMPLE 17

Ethyl 5-(1-p-chlorobenzoyl-5-methoxyindol-2-yl)-2,4-Pentadienoate

A solution of ethyl 5-(5-methoxyindol-2-yl)-2,4-pentadienoate (0.8 g, 2.9 mmol) in 20 ml of tetrahydrofuran (THF) was added dropwise to a suspension of sodium hydride (0.024 g of a 60% reagent) at 0° C. (ice bath). After addition, the mixture was stirred in the ice bath for 1 hour and a solution of p-chlorobenzoyl chloride (0.54 g) in 10 ml of THF was added; the resulting mixture was filtered to remove the precipitate and the filtrate was washed with brine, dried (magnesium sulfate) and concentrated on rotary evaporator to give a yellow oil. Crystallization of this oily substance from acetone-ether afforded 0.75 g of ethyl 5-(1-p-chlorobenzoyl-5-methoxyindol-2-yl)-2,4-pentadienoate as yellow powders, m.p., 121°–125° C. MS(EI): 40 g(M+), 336 (M+—CO$_2$Et).

EXAMPLE 18

2-Methyl-4-(2,4-dibenzyloxyphenyl)-2-Buten-1-ol

A mixture of 7.5 g (0.039 mol) of 1-bromo-2,3-dihydroxybenzene, 11.2 g (0.082 mol) of K$_2$CO$_3$, and 14 g (0.082 mol) of benzyl bromide in 70 ml of acetone was stirred at room temperature overnight, or until all starting material disappeared as indicated by TLC. The reaction mixture was poured into water and the aqueous solution was extracted with ether. The organic layer was separated, dried over MgSO$_4$ and concentrated to give 14.5 g product as white solid.

This compound, 1-bromo-2,4-dibenzyloxybenzene, as formed in accordance with the above procedure is conveniently summarized by the following reaction:

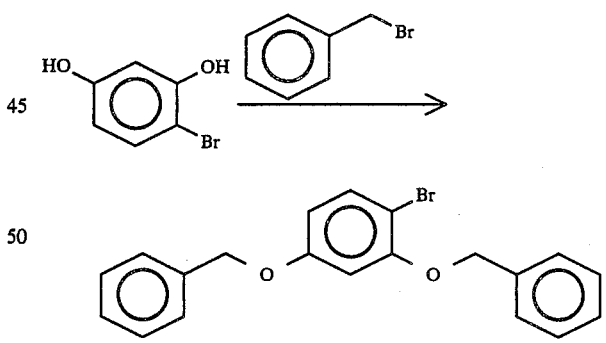

A solution of 5.5 g (0.015 mol) of 1-bromo-2,4-dibenzyloxybenzene and 3.7 g (0.025 mol) of CH$_3$I in 20 ml of ether was added dropwise to 950 mg of Mg turning. The reaction mixture was refluxed for 2 hours and then cooled to −10° C. One gram of CuI was added, and stirring was continued at −10° C. for 30 min. A solution of 3.5 g (01042 mol) of 3-methyl-3,4-epoxy-1-butene in 10 ml of ether was then added dropwise to the reaction mixture, and stirring continued for another hour at −10° C. The reaction was quenced by satd. NH$_4$Cl solution. The organic layer was separated, dried over MgSO$_4$ and concentrated. Purification of the crude product by dry column chromatography gave 1.6 g of product (a mixture of cis/trans isomer 8:2) as white solid; m.p. 83°–85° C.

The product, 2-methyl-4-(2,4-dibenzyloxyphenyl)-2-buten-1-ol, formed from 1-homo-2,4-dibenzyloxybenzene, is conveniently depicted by the following reaction:

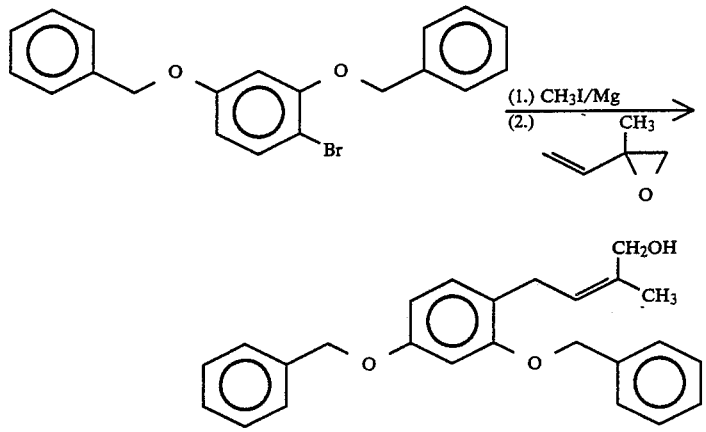

This compound is tabulated in Table 1.

EXAMPLES 19–24

Synthesis of Compounds of the Formula $$(R^1)_{n1}-Ar-X-(CR=CR)_n-[Z(R^2)_{n2}]-(R^3)_{n3}$$

In a manner analogous to the procedure of Example 18, six additional compounds having the generic formula $$R^1{}_{n1}-Ar-X-(CR=CR)_n-[Z(R^2)_{n2}]-(R^3)_{n3}$$

where R, $R^1$, $R^2$, $R^3$, X, Z, Ar, n, $n^1$, $n^2$ and $n^3$ have the meanings given above, were synthesized.

These compounds, identified by their melting point, are summarized, with the compound of Example 18, in Table 1.

TABLE 1

| Compound of Example No. | Structure | MP, °C. |
|---|---|---|
| 18 | 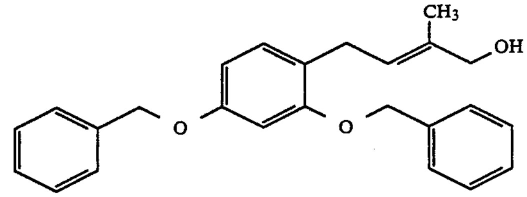 | 83–85 |
| 19 | 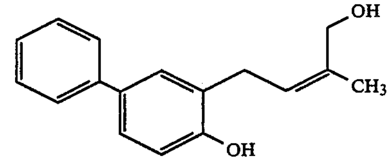 | 94–95 |
| 20 | 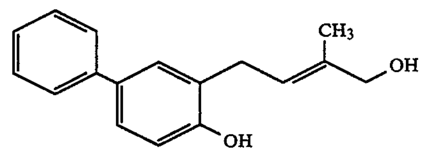 | 128–129 |
| 21 | 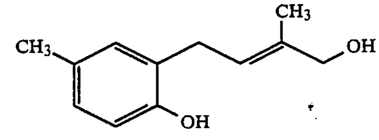 | 97–99 |

TABLE 1-continued

| Compound of Example No. | Structure | MP, °C. |
|---|---|---|
| 22 | 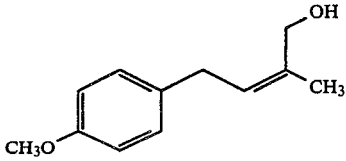 | oil |
| 23 | 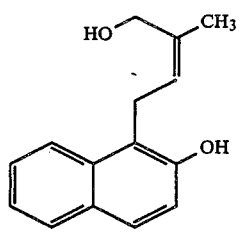 | 161-162 |
| 24 | 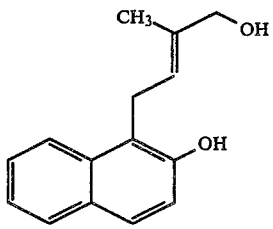 | 127-128 |

The compounds of the present invention have potent activity in regulating the activity of lipoxygenase and as such possess therapeutic value in the treatment of inflammatory conditions and allergic responses such as anaphlaxis and asthma.

Lipoxygenases in mammals have been found in the lung, platelets, and white cells. They are enzymes capable of oxidizing arachidonic acid into hydroperoxyeicosatetraenoic acids (HPETEs) and their stable products hydroxyeicosatertraenoic acids (HETEs). Lipoxygenases are classified according to the position in the arachidonic acid which is oxygenated. Platelets metabolize arachidonic acid to 12-HETE, while polymorphonuclear (PMN) leukocytes contain 5 and 15 lipoxygenases. It is known that 12-HETE and 5, 12-diHETE are chemotactic for human neutrophils and eosinophils, and may augment the inflammation process. 5-HPETE is known to be a precursor of slow-reacting substance of anaphylaxis (SRS-A). The SRS family of molecules, such as leukotrienes B, C, and D, have been shown to be potent bronchoconstrictors (see, NATURE 288, 484-486 (1980)).

The following protocol describes an assay to detect inhibitors are believed to be capable of modulating the biosynthesis of the leukotrienes, a property believed to be useful in treating asthma and inflammatory disease states.

Protocol for Detecting Inhibitors of the Lipoxygenase Pathway

A suspension of rat neutrophils in buffer is incubated for 3 minutes at 30° C. with [$^{14}$C]-arachidonic acid (AA) and Calcium Ionophore A23187. Citric acid (2M) is used to quench the reaction. Following the addition of a trace amount of ($^3$H)-5-HETE together with an excess of unlabeled 5-HETE to each tube, the mixture is extracted with chloroform/methanol. The organic layer is washed with dilute acid and an aliquot is transferred to glass tubes and dried. The residue is dissolved in a small volume of chloroform and an aliquot is spotted on silica get TLC sheets, which are developed with an ethyl acetate/isooctane/water acetic acid solvent system. The 5-HETE spots are visualized with iodine, cut out and placed in scintillation vials for counting. After adjusting for the extraction efficiency, the amount (pmole) of [$^{14}$C]-5-HETE in each of the tubes is quantitated. The net pmoles of 5-HETE are obtained by subtracting the pmoles of 5-HETE in the tubes containing buffer and cells (control). The ability of the test compounds to modulate the activity of this enzyme is determined by a decrease or increase in the net amount of 5-HETE produced.

Table 2 shows the concentration required for inhibition of the 5-lipoxygenase (5-LOX/$I_{50}$ μM) for representative compounds according to the present invention.

TABLE 2

| Compound of Example | LOX, (RAT PMN) $I_{50}$ (μM) |
|---|---|
| 1 | 10 |
| 2 | 2 |
| 3 | 2 |
| 5 | 2 |
| 6 | 4 |
| 7 | 6 |
| 9 | 2.3 |
| 10 | 12 |
| 11 | 15 |
| 13 | 7.5 |
| 16 | 10 |
| 17 | 10 |

Leukotrienes, the products of the 5-lipoxygenase pathway of arachidonic acid metabolism, are potent contractile agents with a variety of smooth muscle preparation. Thus, it has been hypothesized that the leukotrienes contribute significantly to the patophysiology of asthma. The following protocol describes an in vitro assay used to test compounds which specifically antagonize the actions of leukotrienes.

Protocol for SRS-A (Slow-reacting Substance of Anaphylaxis Antagonists (SALTI)

Peripheral strips of guinea pig lungs are prepared and hung in tissue baths (Metro #ME-5505, 10 ml) according to the published procedure (Pro. Nat'l. Acad. Sci., U.S.A. Volume 77, pp. 4354–4358, 1980). The strips are thoroughly rinsed in Assay Buffer and then connected with surgical silk thread to the support rods from the tissue baths. The rods are adjusted in the baths and the strips connected to the pressure transducers (Grass FT 103 or Gould UC-3). The tissue baths are aerated with 95% oxygen 5% carbon dioxide and maintained at 37° C. The Assay Buffer has been made as follows: For each liter of buffer the following are added to approximately 800 ml of water distilled in glass—6.87 g. NaCl, 0.4 g. KCl, 21. g. NaHCO$_3$,.0.14 g. NaH$_2$PO$_4$.H$_2$O, 0.21 g. MgSO$_4$.7H$_2$O, and 2.0 g. D-glucose. Then a solution of 0.368 g. CaCl$_2$.2H$_2$O in 100 ml glass-distilled water is slowly added to the buffer. Sufficient water is added to adjust the volume to one liter, and the solution is aerated with 95% oxygen—5% carbon dioxide. Usually 10 liters of buffer are used for an experiment with 4 tissues.

After the tissues have been repeatedly washed and allowed to equilibrate in the tissue bath, they are challenged with 1 μM histamine. After maximum contractions have been obtained, the tissues are washed, and allowed to relax back to baseline tension. This histamine challenge procedure is repeated at least 1 to 2 more times to obtain a repeatable control response. The average response to 1 μM histamine for each tissue is used to normalize all other challenges.

Responses of each tissue to a predetermined concentration of leukotriene are then obtained. Usually test compounds are examined initially at 30 μM on resting tension of the tissues without any added agonist or antagonist to determine if the compound has any possible intrinsic activity. The tissues are washed, and the test compound is added again. Leukotriene is added after the desired pre-incubation time. The intrinsic activity of the compounds, and their effect on leukotriene-induced contractions are then recorded.

The concentration required for 50% inhibition of 0.2 μM leukotriene C$_4$-induced contraction of guinea pig peripheral strips for representative compounds of the present invention is shown in Table 3.

TABLE 3

| Compound of Example | SALTI, I$_{50}$ μM |
|---|---|
| 7 | 20 |
| 9 | 18 |
| 10 | 2 |
| 12 | 15 |
| 16 | 53% I at 30 μM |

Some compounds in this invention also display potent activities in regulating phospholipases and as such possesses therapeutic value in the treatment of inflammatory conditions.

Inflammatory responses to a variety of offending stimuli are promoted by products of arachidonic acid metabolism. These products include leukotrienes (SRS-A), prostaglandins, prostacyclin and its metabolites, and thromboxanes. No matter what combination of products results from passage of substrate down the branches of this complex cascade, the initial step involves the release of arachidonic acid from phospholipids or from triglycerides containing this longchain fattyacid (1). The enzymes catalyzing such release of arachidonic acid are:

(a) phospholipase C followed by diglyceride lipase (2);

(b) phospholipase A$_2$, either soluble or membrane-bound (3,4); and (c) a lipase able to degrade triglycerides that contain arachidonic acids (1).

Two assays have been developed to test the ability of the invented compounds on the activity of the phospholipases. In one protocol, a procedure is described for testing the inhibitory effects of these compounds on Phospholipase C (PLC), while the other protocol describes a means for testing the inhibitory effect of these compounds on Phospholipase A$_2$ (PLA$_2$).

A. Protocol For In Vitro Assay For Inhibitors Of Phospholipase C (PLC)

The PLC employed in this screen is obtained by aggregation of purified rat platelets in the presence of CaCl$_2$ and ADP. In the enzyme assay phosphatidylinositol having $^3$H -labeled arachidonate residues at R$_2$ is employed as substrate. PLC acts by cleaving the phosphate ester bond yielding diglyceride as follows:

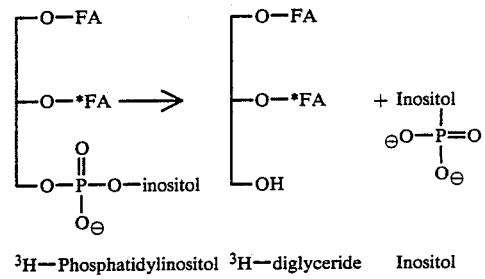

$^3$H—Phosphatidylinositol   $^3$H—diglyceride   Inositol

Following completion of the reaction, the assay medium is acidified and extracted with hexane which takes up unreacted substrate and diglyceride. The hexane extract is passed over a short silica gel column which retains 99% of the phosphatidylinositol. The $^3$H-labeled diglyceride is not retained in scintillation counting vials. The diglyceride is conveniently quantitated by liquid scintillation spectrometry.

The compounds were tested at 300 u in a buffer containing 0.06 mM unlabeled phosphatidylcholine (PC), 20–30,000 cpm of (CPC), 150 mM NaCl, 5 mM CaCl$_2$ and 50 mM tris(hydroxymethyl)methylaminopropane-sulfonic acid buffer, adjusted to pH 9.0 with 1N NaOH. The temperature of the buffer was maintained at a temperature of 37° C. The reaction was initiated by addition of the enzyme and it was terminated 10 minutes later by addition of 1 ml of 1N HCl.

Following acidification, the samples were extracted with 2 ml of isopropyl alcohol and 2 ml of hexane, vortexed and allowed to stand until the phases separate. Free inositol and some unreacted substrate were taken up in the isopropanol-saturated hexane. The hexane phase of the extraction mixture was transferred to a short silica gel column which retains unreacted phosphatidylinositol, but not the 3H-diglyceride. The column effluent was collected directly in scintillation vials. The columns were washed once with additional 2 ml of hexane. The radiolabelled diglycerides were quantitated by liquid scintillation.

REFERENCES

1. Borgeat, P., M. Hamberg, and B. Samuelson. Transformation of arachidonic acid and homo-γ-linolenic acid by rabbit polymorphonuclear leukocytes. J. Biol. Chem., 251: 7816–7810 (1976).
2. Bell, R. L. D. A. Kennerly, N. Stanford, and P. W. Majerus. Diglyceridelipase: A pathway for arachidonate release from platelets. Proc. Nat. Acad. Sci., U.S. 76: 3238–3241 (1979).
3. Vadas, P., and J. B. Hay. The release of phospholipase $A_2$ from aggregated platelets and stimulated macrophases of sheep. Life Sciences, 26: 1721–1729 (1980).
4. Franson, R. C., D. Eisen, R. Jesse, and C. Lanni. Inhibition of highly purified mammalian phospholipases $A_2$ by non-steroidal anti-inflammatory agents, modulation by calcium ions. Biochemical J., 186: 633–636 (1980).

B. In Vitro Assay For Inhibitors of Phospholipase $A_2$ Assayed at pH 7.0 (PLA$_2$)

The PLA$_2$ employed in this screen is obtained by aggregation of purified rat platelets. In the enzyme assay phosphatidylcholine having $^{14}C$-labeled palmitate residues at $R_1$ and $R_2$ is employed as substrate. PLA$_2$ acts by cleaving the $R_2$ fatty acid ester bond yielding free fatty acid and lysophosphatidyl choline as follows:

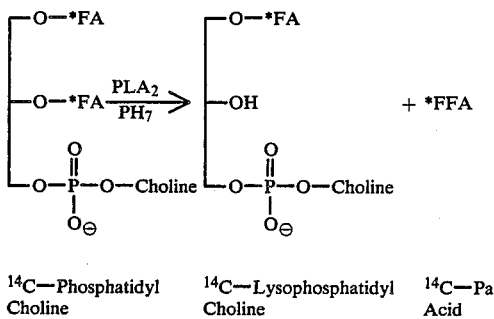

$^{14}C$—Phosphatidyl Choline     $^{14}C$—Lysophosphatidyl Choline     $^{14}C$—Palmitic Acid Following completion of the reaction, the assay medium is acidified and extracted with hexane, which takes up unreacted substrate and free fatty acid product. The hexane extract is passed over a short silica column which retains 99% of the phosphatidyl choline. The $^{14}C$-labeled palmitic acid is not retained (90% recovery in eluate) and is collected directly in scintillation counting vials. The released palmitic acid is conveniently quantitated by liquid scintillation spectrometry.

The compounds were tested at 100 uM in a buffer containing 0.3 mM unlabeled phosphatidylcholine (PC), 20–30,000 cpm of $^{14}C(CPC)$, 100 μM NaCl, 1 mM CaCl$_2$ and 50 mM tris-HCl adjusted to pH 7.2 with 1N NaOH. This resulted in a buffer at pH 7.2. The temperature of the buffer was maintained at a temperature of 37° C. The reaction was initiated by addition of the enzyme and it was terminated 30 minutes later by the addition of 100 ml of 1N HCl.

Following acidification, the samples were extracted with 2 ml of 2-propanol and 2 ml of hexane, vortexed and allowed to stand until the phases separated. Free fatty acids (FFA) and some unreacted substrate were taken up in the isopropanol-saturated hexane. The hexane phase of the extraction mixture was transferred to a short silica gel column which retained reacted PC but not the FFA. The column effluent was collected directly in scintillation vials. The columns were washed once with an additional 2 ml of hexane. The radio labeled FFA were quantitated by liquid scintillation spectrometry.

Another assay has been developed to test the ability of the invented compounds on the activity of cyclooxygenase, which is one of the enzymes metabolizing arachidonic acids. By-products of arachidonic acid metabolism include thromboxanes, a type of which is designated as TXB$_2$, and protoglandins, a class of which is known as PGF$_2\alpha$. As indicated, supra, these by-products promote inflammatory response to a host of offending stimuli. The following protocol describes a procedure for testing the inhibitory effect on the production of TXB$_2$ and PGF$_2\alpha$.

Protocol for Detecting the Production of TXB$_2$ and PGF$_2\alpha$.

A suspension of glycogen elicited rat peritoneal leukocyte-homogenate in buffer is incubated with ($^{14}C$)-arachidonic acid (AA), epinephrine and glutathione for 30 minutes at 37°. The reaction is quenched with 2M citric acid, and a trace amount of ($^3H$)-TXB$_2$ and an excess of unlabeled TXB$_2$ and PGF$_2\alpha$ are added to each tube. After extraction of the mixture with chloroform/methanol, the organic layer is washed with dilute hydrochloric acid followed by evaporation in vacuo. The residue is dissolved in a small volume of chloroform and is spotted on silica gel TLC sheets, which are developed in an ethyl acetate/isooctane/water/acetic acid solvent system. Spots containing TXB$_2$ and PGF$_2\alpha$ are visualized with iodine. Strips containing the spots are cut out, placed in scintillation vials and the radioactive content is quantitated in a liquid scintillation spectrometer.

After adjusting for the extraction efficiency, the amount (pmole) of ($^{14}C$)-TXB$_2$ and PGF$_2\alpha$ in each of the tubes is calculated. The net pmole of product is obtained by subtracting the pmole of TXB$_2$ and PGF$_2\alpha$ in the tubes containing buffer alone (blank) from the pmole of TXB$_2$ and PGF$_2\alpha$ in the tubes containing buffer and cellular homogenate (control). The ability of the test compounds to modulate the activity of this enzyme is determined by a decrease or increase in the net amount of TXB$_2$ and PGF$_2\alpha$ produced.

Compounds of the patent invention also display good activities as PLA$_2$, PLC, and cyclooxygenase inhibitors (Table 4).

TABLE 4

| Compound of Example | Tests and Activities |
|---|---|
| 2 | PLA$_2$, I$_{50}$ = 16 μM |
| 4 | PLA$_2$, I$_{37}$ = 30 μM |
| 7 | PLA$_2$, I$_{42}$ = 30 μM |
| 9 | PLA$_2$, I$_{50}$ = 47 μM |
| 12 | PLA$_2$, I$_{50}$ = 37 μM |
| 9 | PLC, I$_{50}$ = 37 μM |
| 12 | PLC, I$_{50}$ = 40 μM |
| 2 | Cyclox, I$_{37}$ = 100 μM |
| 9 | Cyclox, I$_{50}$ = 15 μM |
| 13 | Cyclox, I$_{32}$ = 100 μM |

The above tests were also applied to the compounds of Formula III, when n=1. The results are indicated in Table 5.

TABLE 5

| Compound | LOX | PLC | PLA$_2$ | SALTI |
| --- | --- | --- | --- | --- |
| Ethyl β-(indol-3-yl)acrylate | $I_{50} = 8$ μM | I | I | M |
| Ethyl-B-(benzylindol-3-yl)acrylate | — | L | L | I |
| B-(1-Benzylindol-3-yl)acrylic acid | M at 3 μM | L | M $I_{44} = 30$ μM | L |
| Ethyl B-(indol-2-yl)acrylate | — | I | — | $I_{50} = 30$ μM |
| Ethyl B-(1-benzyl-2-methyl-indol-3-yl)acrylate | $I_{50} = 1$ μM | I | M | L |
| B-(1-Benzyl-2-methyl-indol-3-yl)acrylic acid | M | — | — | $I_{50} = 20$ μM | where I = inactive
M = moderate activity at level tested
L = low activity at level tested These tests illustrate that when n=1 or n=2 in Formula III, the compounds have therapeutic value in inhibiting the actions of lipoxygenase, phospholipases and cyclooxygenase and in antagonizing the actions of leukotrienes. Thus, these compounds possess therapeutic activity in the treatment of asthma and inflammatory conditions.

The above embodiments and examples are given to illustrate the scope and spirit of the present invention. These embodiments and examples will make apparent, to those skilled in the art, other embodiments and examples. These other embodiments and examples are within the contemplation of the present invention. Therefore, the instant invention should be limited only by the appended claims.

What is claimed is:

1. A compound of the formula

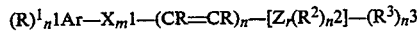

and pharmaceutically acceptable salts thereof;
wherein R$^1$ is independently hydrogen, alkyl, hydroxyalkyl, carboxy, carbalkoxy, carbamoyl, halo, trihalomethyl, hydroxy, alkoxy, aralkoxy, aryloxy, nitro, sulfamoyl, or alkylthio;
Ar is indolyl;
X is alkylene containing up to 4 carbon atoms in the principal chain and up to a total of 6 carbon atoms;
R is hydrogen, or alkyl;
Z is alkylene containing up to 3 carbon atoms in the principal chain and up to a total of 6 carbon atoms;
R$^2$ is a substituent attached to one of the carbons of Z and is oxo, or —OR$^4$;
R$^3$ is hydrogen, —OR$^4$, trifluoromethyl, dialkylamino, carbalkoxy or aryl;
R$^4$ is hydrogen, alkyl, aryl or aralkyl;
m$^1$ is 0 or 1;
n is 1 or 2;
n$^1$ is 1, or 2;
n$^2$ is 1 or 2;
n$^3$ is 0, 1 or 2; and
r is 0 or 1.

2. A therapeutic composition comprising the compound of claim 1 and an inert pharmaceutical carrier.
3. A method of treating hypersensitive, inflammatory conditions, and allergic responses in a mammal comprising administering to said mammal a therapeutically effective amount of the compound of claim 1.
4. 5-(1-Benzylindol-3-yl)-2,4-pentadienoic acid.
5. N-(4-Carbethoxyphenyl)-5-(1-benzyloxyindol-3-yl)-2,4-pentadienoamide.
6. Ethyl 5-(1-benzyl-5-benzyloxyindol-3-yl)-2,4-pentadienoate.
7. Ethyl 5-(1-Benzyl-5-methoxyindol-3-yl)-2,4-pentadienoate.
8. Ethyl 5-(1-benzylindol-3-yl)-2-ethyl-2,4-pentadienoate.
9. 5-(1-Benzylindol-3-yl)-2-ethyl-2,4-pentadienoic acid.
10. Ethyl 5-(1-p-chlorobenzoylindol-3-yl)-2,4-pentadienoic acid.
11. 5-(1-Benzyl-2-methylindol-3-yl)-2,4pentadienoic acid.
12. 1-Benzyl-3-(3-hydroxy-1-propen-1-yl)-indole.
13. 5-(1-Benzylindol-3-yl)-2,4-pentadien-1-al.
14. 1-Benzyl-3(4-hydroxy-1,3-decadien-1-yl)-indole.
15. 5-(1-Benzylindol-3-yl)-2-propyl-2,4-pentadienoic acid.
16. 5-(1-Benyzlindol-3-yl)-2-methyl-2,4-pentadienoic acid.
17. 5-(1-Benzyl-5-chloroindol-3-yl)-2,4-pentadienoic acid.
18. Ethyl 5-(5-methoxyindol-2-yl)-2,4-pentadienoate.
19. Ethyl 5-(1-p-chlorobenzoyl-5-methoxyindol-2-yl)-2,4-pentadienoate.
20. Ethyl 5-(1-p-chlorobenzoylindol-3-yl)-2,4-pentadienoate.
21. The compound according to claim 1 wherein X is methylene.
22. The compound according to claim 1 wherein each R is hydrogen or methyl.
23. The compound according to claim 1 wherein n$^3$ is 1.
24. The compound according to claim 1 wherein Z is methylene.

* * * * *